(12) United States Patent
Fang et al.

(10) Patent No.: US 10,655,060 B2
(45) Date of Patent: May 19, 2020

(54) PREPARATION METHOD AND APPLICATION OF FLUORESCENT COMPOUND HAVING SENSING ABILITY TO ANILINE AND O-TOLUIDINE GAS, AND FLUORESCENT FILM WITH THE SAME

(71) Applicant: SHAANXI NORMAL UNIVERSITY, Xi'an, Shaanxi (CN)

(72) Inventors: Yu Fang, Shaanxi (CN); Jiayun Fan, Shaanxi (CN); Ke Liu, Shaanxi (CN); Xingmao Chang, Shaanxi (CN); Haonan Peng, Shaanxi (CN); Meixia He, Shaanxi (CN); Congdi Shang, Shaanxi (CN); Gang Wang, Shaanxi (CN)

(73) Assignee: SHAANXI NORMAL UNIVERSITY, Xi' an, Shaanxi (CN)

( * ) Notice: Subject to any disclaimer, the term of this patent is extended or adjusted under 35 U.S.C. 154(b) by 0 days.

(21) Appl. No.: 15/780,635

(22) PCT Filed: Nov. 29, 2016

(86) PCT No.: PCT/CN2016/107719
§ 371 (c)(1),
(2) Date: Sep. 28, 2018

(87) PCT Pub. No.: WO2017/201998
PCT Pub. Date: Nov. 30, 2017

(65) Prior Publication Data
US 2019/0062629 A1 Feb. 28, 2019

(30) Foreign Application Priority Data
May 23, 2016 (CN) .......................... 2016 1 0345255

(51) Int. Cl.
| | | |
|---|---|---|
| *C09K 11/06* | (2006.01) | |
| *C07D 471/06* | (2006.01) | |
| *G01N 31/22* | (2006.01) | |
| *G01N 21/64* | (2006.01) | |
| *G01N 21/84* | (2006.01) | |

(52) U.S. Cl.
CPC ............ *C09K 11/06* (2013.01); *C07D 471/06* (2013.01); *G01N 21/6428* (2013.01); *G01N 31/22* (2013.01); *G01N 31/223* (2013.01); *C09K 2211/1018* (2013.01); *G01N 21/643* (2013.01); *G01N 21/8483* (2013.01)

(58) Field of Classification Search
CPC ............ C09K 11/06; C09K 2211/1029; C09K 2211/1018; C09K 2211/1014; C09K 2211/1007; G01N 31/22; G01N 31/223; G01N 21/6428; G01N 21/643; G01N 21/8483; C07D 471/06
See application file for complete search history.

(56) References Cited

PUBLICATIONS

Fan, J., "Functionality-oriented derivatization of naphthalene diimide: a molecular gel strategy-based fluorescent film for aniline vapor detection." ACS applied materials & interfaces 8.28 (2016): 18584-18592.*

Fan, J., "Functionality-oriented derivatization of naphthalene diimide: a molecular gel strategy-based fluorescent film for aniline vapor detection." ACS applied materials & interfaces 8.28 (2016): 18584-18592; Supporting Information: S1-S19.*

Scriven, L. E., "Physics and applications of dip coating and spin coating." MRS Online Proceedings Library Archive 121 (1988).*

Perlich, J., "Solvent content in thin spin-coated polystyrene homopolymer films." Macromolecules 42.1 (2008): 337-344.*

Che, Y., "Expedient vapor probing of organic amines using fluorescent nanofibers fabricated from an n-type organic semiconductor." Nano letters 8.8 (2008): 2219-2223.*

* cited by examiner

*Primary Examiner* — John M Mauro (57) ABSTRACT

The present invention discloses a fluorescent compound having a sensing ability to aniline and o-toluidine, a preparation method thereof, a preparation method and application of a fluorescent sensing film. The compound contains a naphthalenediimide (NDI) unit, two alkynyl aniline conjugate fragments and two long alkyl chain fragments; compared with perylene anhydride (PDI), naphthalenediimide (NDI) has better solubility, rich photophysical property, good photochemical stability and strong π-π stacking effect; these building units make the prepared fluorescent compound have supramolecular characteristics and more abundant gelling behavior and assembly behavior. Therefore, the sensing film prepared with the fluorescent compound is controllable in the microstructure, good in stability, high in sensitivity, long in service life and able to be repeatedly used. The present invention achieves the sensitive detection of aniline, and more importantly, the detection is completely reversible, so as to lay the solid foundation for the realization of aniline fluorescence sensor.

9 Claims, 2 Drawing Sheets

PREPARATION METHOD AND APPLICATION OF FLUORESCENT COMPOUND HAVING SENSING ABILITY TO ANILINE AND O-TOLUIDINE GAS, AND FLUORESCENT FILM WITH THE SAME

CROSS REFERENCE OF RELATED APPLICATION

This is a U.S. National Stage under 35 U.S.C 371 of the International Application PCT/CN2016/107719, filed Nov. 29, 2016, which claims priority under 35 U.S.C. 119(a-d) to CN 201610345255.0, filed May 23, 2016.

BACKGROUND OF THE PRESENT INVENTION

Field of Invention

The present invention relates to a technical field of fluorescent compound preparation, and relates to a fluorescent compound, a preparation method thereof, a preparation method and application of a fluorescent sensing film with the same, and more particularly to a preparation method and application of a fluorescent compound having a sensing ability to aniline and o-toluidine, and a fluorescent sensing film with the same.

Description of Related Arts

Organic amine gases are by-products of cell growth and biological decay, and meanwhile, as an important chemical raw material, organic amines are also widely used in the fields of chemical production, cosmetics research and development and food additives, which also means that organic amine gases can be released from many areas such as landfills, waste water, automotive exhaust and industrial waste. Excess organic amine gases seriously damage the ecological environment and people's health. Some organic amine gases are often used as air quality indicators and some are also used for monitoring certain diseases such as uremia, liver disease and lung cancer. At present, the content of aniline and o-toluidine in most chemical plants far exceeds the range that the human body can bear. The presence of excess aniline and o-toluidine significantly increases the risk of methemoglobinemia. Therefore, fast and accurate detection for the aniline in the environment and air is imminent.

In order to effectively monitor the air quality, developing a rapid, accurate and sensitive method for on-site detection of aniline has become a major research topic for researchers and public security departments. Currently, there are mainly two methods comprising photometry and chromatography to monitor aniline in the environment, but the two methods are very harsh in monitoring conditions and expensive in cost, so that the two methods are difficult to be widely used. Therefore, many researchers have developed the fluorescence method, flow injection spectrophotometry and kinetic spectrophotometry to measure the aniline. Among them, the fluorescence method, which obtains the thin film fluorescence sensor by fixing fluorescence reporting groups to the surface of the solid substrate, is reusable and easy to prepare devices. Therefore, for the gas phase detection of organic amines, it is very significant to develop the high-performance fluorescent thin film sensor. Although the detection of organic amines is getting more and more attention, in the currently reported sensing system, the sensitivity and selectivity are difficult to meet actual testing needs.

SUMMARY OF THE PRESENT INVENTION

To overcome deficiencies in the prior art, the purpose of the present invention is to provide a kind of fluorescent compounds with sensing function for aniline and o-toluidine and their preparation and application of fluorescent sensing film. The preparation method of the fluorescent compound is simple in operation and good in stabilization. The fluorescent sensing film prepared with the fluorescent compound has advantages such as high sensitivity and rapid response speed while being detected, and is able to effectively and quickly detect the aniline and o-toluidine gas.

The present invention is achieved through technical solutions as follows.

The present invention provides a fluorescent compound having a sensing ability to aniline and o-toluidine, the structural formula of the fluorescent compound is shown below:

wherein:

Also, the present invention provides a method for preparing a fluorescent compound having a sensing ability to aniline and o-toluidine, which comprises steps of:

(1) preparing a first compound, which comprises:
dissolving 1,4,5,8-naphthalenetetracarboxylic dianhydride and dibromo isocyanuric acid into a first amount of oleum with a concentration of 20% and a second amount of oleum with a concentration of 20%, respectively, and then sufficiently uniformly stirring at room temperature, adding the second amount of oleum dissolved with the dibromo isocyanuric acid into the first amount of oleum dissolved with the 1,4,5,8-naphthalenetetracarboxylic dianhydride drop by drop, and then continuously stirring and reacting at 60-90° C. for 12-48 h, mixing, obtaining a mixed solution, uniformly stirring after pouring the mixed solution into crushed ice, and then vacuum filtering, washing, drying, and obtaining the first compound, wherein: a structural formula of the first compound is (2) preparing a second compound, which comprises:

dissolving the first compound into glacial acetic acid under nitrogen protection, and then uniformly stirring at room temperature, and then adding a seventh compound, reflux-stirring for 2-4 h, filtering and collecting a precipitate, dissolving the precipitate into ice water and sufficiently stirring, and then vacuum filtering, washing, drying, performing column chromatography separation, and obtaining the second compound, wherein: a structural formula of the second compound is a structural formula of the seventh compound is R—NH$_2$,

(3) preparing a third compound, which comprises:

dissolving the second compound, benzenamine,4-ethynyl-, tetrakistriphenylphosphine palladium and cuprous iodide into a mixed solvent of toluene and diisopropylamine under water-free and oxygen-free condition, and then stirring and reacting at 50-70° C. for 24-48 h, respectively, and extracting with saturated sodium chloride aqueous solution and water, spin-drying, performing column chromatography separation, and obtaining the third compound, wherein a structural formula of the third compound is (4) preparing a fourth compound, which comprises:

dissolving methyl trihydroxybenzoate into N,N-dimethylformamide under water-free and oxygen-free condition, and then adding potassium carbonate and potassium iodide in sequence, adding brominated alkane after stirring at 80-120° C. for 30 min, continuously reflux-stirring for 24-48 h, filtering and collecting a precipitate, vacuum filtering and washing the precipitate, obtaining a filtrate, refrigerating the filtrate, and then separating white solid out, and obtaining the fourth compound, wherein a structural formula of the fourth compound is n=12 or 16;

(5) preparing a fifth compound, which comprises:

dissolving the fourth compound into ethanol, and then adding potassium hydroxide, reflux-stirring and reacting for 8-12 h, diluting a stirred and reacted solution with water, adjusting a pH value to 1, filtering and collecting a precipitate, vacuum filtering, washing and drying the precipitate, and obtaining the fifth compound, wherein a structural formula of the fifth compound is (6) preparing a sixth compound, which comprises:

adding the fifth compound into toluene under nitrogen protection, and then adding a catalytic amount of thionylchloride (SOCl$_2$), reflux-stirring and reacting for 4 h, and then removing excess thionylchloride (SOCl$_2$) and toluene, and obtaining the sixth compound, wherein a structural formula of the sixth compound is and (7)

dissolving the sixth compound, N1-((ethylimino)methylene)-N3,N3-dimethylpropane-1,3-diamine (EDC) and 4-dimethylaminopyridine (DMAP) into redistilled toluene solution under nitrogen protection, and then adding the third compound after stirring and reacting for 30 min, continuously stirring and reacting at room temperature for 12-20 h, and then washing with water, obtaining a reacted solution, drying after removing solvent from the reacted solution, performing column chromatography separation, and finally obtaining the fluorescent compound, wherein a structural formula of the fluorescent compound is In the step (1), a molar ratio of the 1,4,5,8-naphthalenetetracarboxylic dianhydride to the dibromo isocyanuric acid is 1:(1-1.5), a molar ratio of the first amount of oleum to the second amount of oleum is 1:1.

In the step (2), a molar ratio of the first compound, the seventh compound and the glacial acetic acid is 1:(2.5-3):(300-400); the column chromatography separation is performed using an eluent prepared by mixing dichloromethane and petroleum ether with a volume ratio of 1:1.

In the step (3), a molar ratio of the second compound, the benzenamine,4-ethynyl-, the tetrakistriphenylphosphine palladium and the cuprous iodide is 1:(2-3):(0.05-0.1):(0.05-0.1); a volume ratio of the toluene to the diisopropylamine in the mixed solvent is 7:3; the column chromatography separation is performed using an eluent prepared by mixing tetrahydrofuran and petroleum ether with a volume ratio of 1:3.

In the step (4), a molar ratio of the methyl trihydroxybenzoate, the brominated alkane reagent, the potassium carbonate, the potassium iodide and the N,N-dimethylformamide is 1:(3-5):(10-15):0.05:(80-100); the pH value is adjusted through hydrochloric acid with a concentration of 1 mol/L.

In the step (5), a molar ratio of the fourth compound, the potassium hydroxide and the ethanol is 1:(2-3):(350-400).

In the step (6), a molar ratio of the fifth compound, the thionylchloride (SOCl$_2$) and the toluene is 1:(5-10):(1000-1500).

In the step (7), a molar ratio of the third compound, the sixth compound, the EDC and the DMAP is 1:(1.5-3):(0.1-0.2):(0.2-0.4), the column chromatography separation is performed using dichloromethane as an eluent.

Also, the present invention provides a method for preparing a fluorescent sensing film with the prepared fluorescent compound having the sensing ability to aniline and o-toluidine, which comprises steps of:

(1) dissolving the fluorescent compound having the sensing ability to the aniline and the o-toluidine into methyl cyclohexane, and obtaining a stock solution with a concentration of 5×10 mol/L; and (2) uniformly spin-coating the stock solution onto a surface of a glass substrate, and then standing for 4-12 h. and obtaining the fluorescent sensing film, wherein the fluorescent compound has a structural formula of:

here,

Also, the present invention provides an application of the fluorescent sensing film in preparing a fluorescent sensing device.

Compared with the prior art, the present invention has beneficial effects as follows.

The present invention discloses a fluorescent compound having a sensing ability to aniline and o-toluidine, which contains a naphthalenediimide (NDI) unit, two alkynyl aniline conjugate fragments and two long alkyl chain fragments; compared with perylene anhydride (PDI), the core structure of naphthalenediimide (NDI) has better solubility, rich photophysical property, good photochemical stability and strong π-π stacking effect; these building units make the prepared fluorescent compound have supramolecular characteristics and more abundant gelling behavior and assembly behavior. Therefore, the film prepared with this kind of fluorescent compound is controllable in the microstructure and good stability on the glass substrates.

The present invention also discloses a preparation method of the fluorescent compound having the sensing ability to aniline and o-toluidine, which is simple in operation, easy to obtain raw materials and good in stability, has controllable reaction and friendly environment, and is adapted for mass production.

The present invention also discloses a method of preparing a fluorescent sensing film with the above fluorescent compound, which comprises physically coating naphthalenediimide (NDI) derivative onto a surface of a glass substrate, so as to obtain the fluorescent sensing film with fast response and complete reversibility. The sensing film has high fluorescence quantum yield, good photochemical stability and ultrafine fibered network micro-topography. The larger specific surface area and the dense network structure of the sensing film are conducive to the capture and adsorption of aniline, for further sensing the aniline and the o-toluidine, and meanwhile greatly improving response to aniline and o-toluidine vapors. Therefore, the present invention has high sensitivity to the detection of aniline gas and is expected to find potential application in chemical plants and large crude oil companies.

DETAILED DESCRIPTION OF THE PREFERRED EMBODIMENT

The present invention is further described in detail with specific embodiments as follows, which are explanation but not limitation to present invention.

A fluorescent compound having a sensing ability to aniline and o-toluidine provided by the present invention is prepared by steps of:

(1) preparing a first compound, which comprises:

dissolving 1,4,5,8-naphthalenetetracarboxylic dianhydride and dibromo isocyanuric acid in a first amount oleum with a concentration of 20% and a second amount oleum with a concentration of 20%, respectively, and then sufficiently uniformly stirring at room temperature for 2 h, adding the second amount of oleum dissolved with the dibromo isocyanuric acid into the first amount of oleum dissolved with the 1,4,5,8-naphthalenetetracarboxylic dianhydride drop by drop, continuously stirring and reacting at 90° C. for 12-48 h, mixing, obtaining a mixed solution, uniformly stirring after pouring the mixed solution into crushed ice, vacuum filtering, washing with water and drying, and obtaining the first compound, wherein:

a structural formula of the first compound is a molar ratio of the 1,4,5,8-naphthalenetetracarboxylic dianhydride to the dibromo isocyanuric acid is 1:(1-1.5), a molar ratio of the first amount of oleum to the second amount of oleum is 1:1, a reaction equation is shown below:

(2) preparing a second compound, which comprises:

dissolving the first compound into glacial acetic acid under nitrogen protection, stirring at room temperature for 30 min, and then adding a seventh compound, continuously stirring at 120° C. for 2-4 h, obtaining a precipitate, dissolving the precipitate into ice water and stirring for 30 min, vacuum filtering, washing with water and drying, performing column chromatography separation and obtaining the second compound, wherein:

a structural formula of the second compound is a structural formula of the seventh compound is R—NH$_2$, a molar ratio of the first compound and the seventh compound is 1:(2.5-3), the column chromatography separation is performed with an eluent prepared by mixing dichloromethane and petroleum ether with a volume ratio of 1:1, and a reaction equation is shown below:

(3) preparing a third compound, which comprises:

dissolving the second compound, benzenamine,4-ethynyl-, tetrakistriphenylphosphine palladium and cuprous iodide into a mixed solvent of toluene and diisopropylamine under water-free and oxygen-free condition, stirring and reacting at 70° C. for 24-48 h, drying a stirred and reacted intermediate product in a hanging manner, performing column chromatography separation, and obtaining the third compound, wherein:

a structural formula of the third compound is a molar ratio of the second compound, the benzenamine, 4-ethynyl-, the tetrakistriphenylphosphine palladium, the cuprous iodide, the toluene and the diisopropylamine is 1:(2-3):(0.05-0.1):(0.05-0.1):(800-1000):(300-500), the column chromatography separation is performed with an eluent prepared by mixing tetrahydrofuran and petroleum ether with a volume ratio of 1:3, and a reaction equation is to shown below:

(4) preparing a fourth compound, which comprises:

dissolving methyl trihydroxybenzoate into N,N-dimethylformamide under water-free and oxygen-free condition, adding potassium carbonate and potassium iodide in sequence, adding brominated alkane after stirring at 120° C. for 2 h, continuously stirring at 150° C. for 24-48 h, obtaining a precipitate, washing with ethyl acetate after vacuum filtering the precipitate, obtaining a filtrate, refrigerating the filtrate, separating white solid out, and obtaining the fourth compound, wherein:

a structural formula of the fourth compound is n=12 or 16;

a molar ratio of the methyl trihydroxybenzoate, the brominated alkane reagent, the potassium carbonate, the potassium iodide and the N,N-dimethylformamide is 1:(3-5):(10-15):0.5:(80-100), a reaction equation is shown below:

(5) preparing a fifth compound, which comprises:

dissolving the fourth compound in ethanol, and then adding potassium hydroxide, reflux-stirring at 80° C. for 8 h, diluting a stirred solution with water, acidizing with a certain concentration of hydrochloric acid to pH=1, obtaining a precipitate, vacuum filtering, washing with water and drying the precipitate, and obtaining the fifth compound, wherein:

a structural formula of the fifth compound is a molar ratio of the fourth compound, the potassium hydroxide and the ethanol is 1:(2-3):(350-400), a concentration of the hydrochloric acid is 1 mol/L, a reaction equation is shown below:

(6) preparing a sixth compound, which comprises:

adding the fifth compound into toluene under nitrogen protection, and then adding a catalytic amount of thionylchloride ($SOCl_2$), reflux-stirring for 4 h, removing excess thionylchloride ($SOCl_2$) and toluene, and obtaining the sixth compound, wherein:

a structural formula of the sixth compound is a molar ratio of the fifth compound, the thionylchloride ($SOCl_2$) and the toluene is 1:(5-10):(1000-1500), a reaction equation is shown below:

and (7) dissolving the sixth compound, N1-((ethylimino)methylene)-N3,N3-dimethylpropane-1,3-diamine (EDC) and 4-dimethylaminopyridine (DMAP) into redistilled toluene solution under nitrogen protection, stirring for 30 min, adding the third compound into a mixed solution, continuously stirring and reacting at room temperature for 12 h, washing with water, and then removing solvent from a reacted solution, drying, performing column chromatography separation, and finally obtaining the fluorescent compound, wherein:

a structural formula of the fluorescent compound is a molar ratio of the third compound, the sixth compound, the EDC and the DMAP is 1:(1.5-3):(0.1-0.2):(0.2-0.4), the column chromatography separation is performed with an eluent prepared by dichloromethane, a reaction equation is shown below:

In the step (1), when bis-brominated naphthalenediimide (NDI) derivative is synthetized, the preferably molar ratio of the 1,4,5,8-naphthalenetetracarboxylic dianhydride to the dibromo isocyanuric acid is 1:1, the molar ratio of the first amount of oleum to the second amount of oleum is 1:1.

In the step (2), when paraffin-bis-brominated naphthalenediimide (NDI) derivative is synthetized, the preferably molar ratio of the first compound, the seventh compound and the acetic acid is 1:2.5:360; the column chromatography separation is performed with the eluent prepared by mixing dichloromethane and petroleum ether with the volume ratio of 1:1.

In the step (3), when primary amine and naphthalenediimide (NDI) conjugated derivative fragments are synthesized, the preferably molar ratio of the second compound, the benzenamine,4-ethynyl-, the tetrakistriphenylphosphine palladium, the cuprous iodide, the toluene and the diisopropylamine is 1:2.5:0.05:0.05:920:300, the column chromatography separation is performed with the eluent prepared by mixing tetrahydrofuran with petroleum ether with the volume ratio of 1:3.

In the step (4), when alkyl methylformate is synthesized, the preferably molar ratio of the methyl trihydroxybenzoate, the brominated alkane reagent, the potassium carbonate, the potassium iodide and the N,N-dimethylformamide is 1:3:10:0.05:80.

In the step (5), when alkyl carboxylic acid is synthesized, the preferably molar ratio of the fourth compound, the potassium hydroxide and the ethanol is 1:2:380.

In the step (6), when alkyl acyl chloride is synthesized, the preferably molar ratio of the fifth compound, the thionylchloride ($SOCl_2$) and the toluene is 1:5:1000.

In the step (7), when the long chain modifies a naphthalenediimide (NDI) derivative having a conjugated structure, the preferably molar ratio of the third compound, the sixth compound, the EDC and the DMAP is 1:1.5:0.1:0.2, the eluent for the column chromatography separation is dichloromethane.

Also, the present invention provides a method for preparing a fluorescent sensing film with the prepared fluorescent compound, which comprises steps of:

dissolving the fluorescent compound having a sensing ability to aniline and o-toluidine into methyl cyclohexane, obtaining stock solutions with different concentrations, uniformly spin-coating the stock solution with a volume of 5 μL-25 μL onto a clean and activated glass substrate surface, and then standing at room temperature for 4-12 h, and then naturally drying at room temperature for 24 h, obtaining the fluorescent sensing film, sealing the fluorescent sensing film for standby application.

Preferably, the method comprises steps of: dissolving the fluorescent compound having the sensing ability to aniline and o-toluidine into methyl cyclohexane, obtaining a stock solution with a concentration of $5\times10^{-4}$ mol/L, uniformly spin-coating the stock solution with the volume of 15 μL onto the clean and activated glass substrate surface, and then standing at room temperature for 6 h, and then naturally drying at room temperature for 24 h, obtaining the fluorescent sensing film, sealing for standby application.

The glass substrate is activated by steps of:
cutting a glass plate into a glass piece with a size of 4 cm×0.5 cm, immersing the glass piece into a newly prepared chromic acid solution for 1-3 days, rinsing thoroughly with a large amount of secondary water after taking out the immersed glass piece, immersing into a mixed solution prepared by mixing $H_2SO_4$ with a mass fraction of 98% and $H_2O_2$ with a mass fraction of 30% with a volume ratio of 3:1 after drying the rinsed glass piece, heating the mixed solution to a temperature of 80-100° C., and then activating the glass pieces for 1-3 h, rinsing with a large amount of secondary water after naturally cooling the activated glass piece to room temperature, drying and obtaining the clean and activated glass substrate.

First Embodiment

A method for preparing a fluorescent sensing film having a sensing ability to aniline and o-toluidine according to a first embodiment of the present invention comprises steps of:

(1) respectively dissolving 0.57 g of 1,4,5,8-naphthalenetetracarboxylic dianhydride and 0.62 g of dibromo isocyanuric acid into 50 mL of oleum with a concentration of 20%, and then sufficiently uniformly stirring at room temperature for 2 h, adding the oleum dissolved with the dibromo isocyanuric acid into the oleum dissolved with the 1,4,5,8-naphthalenetetracarboxylic dianhydride drop by drop for 1 h, and then continuously stirring and reacting at 90° C. for 24 h, obtaining a mixed solution, uniformly stirring for 30 min after pouring the mixed solution into crushed ice, and then sucking and filtering an obtained precipitate, drying under vacuum after washing a sucked and filtered intermediate product with water for 3 times, and obtaining a first compound, wherein: a molar ratio of the 1,4,5,8-naphthalenetetracarboxylic dianhydride to the dibromo isocyanuric acid is 1:1, and a molar ratio of the oleum dissolved with the dibromo isocyanuric acid to the oleum dissolved with the 1,4,5,8-naphthalenetetracarboxylic dianhydride is 1:1, (2) dissolving 0.1 g of the first compound into 25 mL of glacial acetic acid under nitrogen protection, and then stirring at room temperature for 30 min, adding 100 μL of a seventh compound after sufficiently dissolving the first compound, continuously stirring at 120° C. for 3 h, dissolving an obtained precipitate into ice water and stirring for 30 min, sucking and filtering an obtained solid precipitate, drying under vacuum after washing a sucked and filtered intermediate product with water for 3 times, and then performing column chromatography separation, and obtaining a second compound, wherein: a molar ratio of the first compound, the seventh compound and the glacial acetic acid is 1:2.5:360, the column chromatography separation is performed with an eluent prepared by mixing dichloromethane and petroleum ether with a volume ratio of 1:1, in here, n is equal to 12, the seventh compound is m=4;

(3) dissolving 0.09 g of the second compound, 0.049 g of benzenamine,4-ethynyl-, 0.001 g of tetrakistriphenylphosphine palladium and 0.00132 g of cuprous iodide into a mixed solvent of 14 mL of toluene and 6 mL of diisopropylamine under water-free and oxygen-free condition, and then stirring and reacting at 70° C. for 48 h, washing an obtained mixture with saturated ammonium chloride solution for 3 times, and then washing with saturated sodium bicarbonate solution for 3 times, and then washing with saturated sodium chloride aqueous solution for 3 times, drying under vacuum after drying a washed intermediate product in a hanging manner, and then performing column chromatography separation, and obtaining a third compound, wherein:

a preferable molar ratio of the second compound, the benzenamine,4-ethynyl-, the tetrakistriphenylphosphine palladium, the cuprous iodide, the toluene and the diisopropylamine is 1:2.5:0.05:0.05:920:300, the column chromatography separation is performed with an eluent prepared by mixing tetrahydrofuran with petroleum ether with a volume ratio of 1:3;

(4) dissolving 2 g of methyl trihydroxybenzoate into 50 mL of N,N-dimethylformamide under water-free and oxygen-free condition, and then adding 15 g of potassium carbonate and 0.2 g of potassium iodide in sequence, adding 10 mL of brominated alkane reagent after stirring at 120° C. for 2 h, continuously stirring at 150° C. for 48 h, obtaining a precipitate, washing with ethyl acetate for 3 times after sucking and filtering the precipitate, obtaining a filtrate, refrigerating the filtrate, and then separating white solid out, and obtaining a fourth compound, wherein:

a molar ratio of the methyl trihydroxybenzoate, the brominated alkane reagent, the potassium carbonate, the potassium iodide and the N,N-dimethylformamide is 1:3:10:0.05:80, in here, n is equal to 12;

(5) dissolving 0.5 g of the fourth compound into 17 mL of ethanol, and then adding 0.4 g of potassium hydroxide, reflux-stirring at 80° C. for 8 h, diluting a stirred solution with water, acidizing a diluted solution with hydrochloric acid having a concentration of 1 mol/L to pH=1, obtaining a precipitate, sucking and filtering the precipitate, drying after washing a sucked and filtered intermediate product with water for 3 times, and obtaining a fifth compound, wherein:

a molar ratio of the fourth compound, the potassium hydroxide and the ethanol is 1:2:380;

(6) adding 0.1 g of the fifth compound into 20 mL of toluene under nitrogen protection, and then adding 1.5 mL of thionylchloride (SOCl$_2$), reflux-stirring for 4 h, removing excess thionylchloride (SOCl$_2$) with toluene for 3 times, and obtaining a sixth compound, wherein:

a molar ratio of the fifth compound, the thionylchloride (SOCl$_2$) and the toluene is 1:5:1000; and (7) dissolving 1.285 g of the sixth compound, 0.34 g of EDC and 0.01 g of DMAP into 25 mL of redistilled toluene solution under nitrogen protection, and then stirring at room temperature for 30 min, obtaining a mixed solution, adding 0.53 g of the third compound into the mixed solution, continuously stirring and reacting at room temperature for 12 h, and then washing with water for 3 times, and then removing solvent from a reacted solution, drying under vacuum, performing column chromatography separation, and finally obtaining the fluorescent compound having the sensing ability to the aniline and the o-toluidine, wherein:

a molar ratio of the third compound, the sixth compound, the EDC and the DMAP is 1:1.5:0.1:0.2, the column chromatography separation is performed with an eluent prepared by dichloromethane.

A method for preparing a fluorescent sensing film with the prepared fluorescent compound, which comprises steps of:

dissolving the compound having the sensing ability to the aniline and the o-toluidine into methyl cyclohexane, obtaining a stock solution with a concentration of $5\times10^{-4}$ mol/L, uniformly spin-coating the stock solution with the volume of 15 μL onto the clean and activated glass substrate surface, and then standing at room temperature for 6 h, and then naturally drying at room temperature for 24 h, and obtaining the fluorescent sensing film for sealing and standby application.

The above glass substrate is activated by steps of:

cutting a glass plate into a glass piece with a size of 4 cm×0.5 cm, immersing the glass piece into a newly prepared chromic acid solution for 1-3 days, rinsing thoroughly with a large amount of secondary water after taking out the immersed glass piece, immersing into a mixed solution prepared by mixing H$_2$SO$_4$ with a mass fraction of 98% and H$_2$O$_2$ with a mass fraction of 30% with a volume ratio of 3:1 after drying the rinsed glass piece, heating the mixed solution to a temperature of 80-100° C., and then activating the glass pieces for 1-3 h, rinsing with a large amount of secondary water after naturally cooling the activated glass piece to room temperature, drying and obtaining the clean and activated glass substrate.

Nuclear magnetic hydrogen spectrum data of the prepared fluorescent compound are: $^1$H NMR (6 ppm, 600 MHz, CDCl$_3$): 8.88 (s, 2H, naphthalene), 7.82 (s, 2H, NH), 7.74-7.78 (m, 8H, benzene), 7.06 (s, 4H, benzene) 4.16-4.23 (m, 4H, NCH$_2$), 4.02-4.06 (m, 6H, OCH$_2$), 1.99-2.02 (m, 2H, CH), 1.75-1.85 (m, 12H, CH$_2$), 1.27-1.55 (m, 124H, CH$_2$), 0.88-0.98 (m, 30H, CH$_3$). Infrared spectral data thereof are IR (KBr, cm$^{-1}$): 3261 (Ar—N), 2853 (C—H), 2196 (C≡C), 1712 (C=O), 1336 (C—N), 798 (Ar—R). Mass spectrometry data thereof are MS (MALDI-TOF, m/z): calcd for $C_{132}H_{200}N_4O_{12}$, 2035.02; found, 2035.83. Elemental analysis data thereof are Elem. Anal., calc. for $C_{132}H_{200}N_4O_{12}$ (%): C, 77.91; H, 9.91; N, 2.75. Found: C, 78.05; H, 9.79; N, 2.55.

Figure 1:
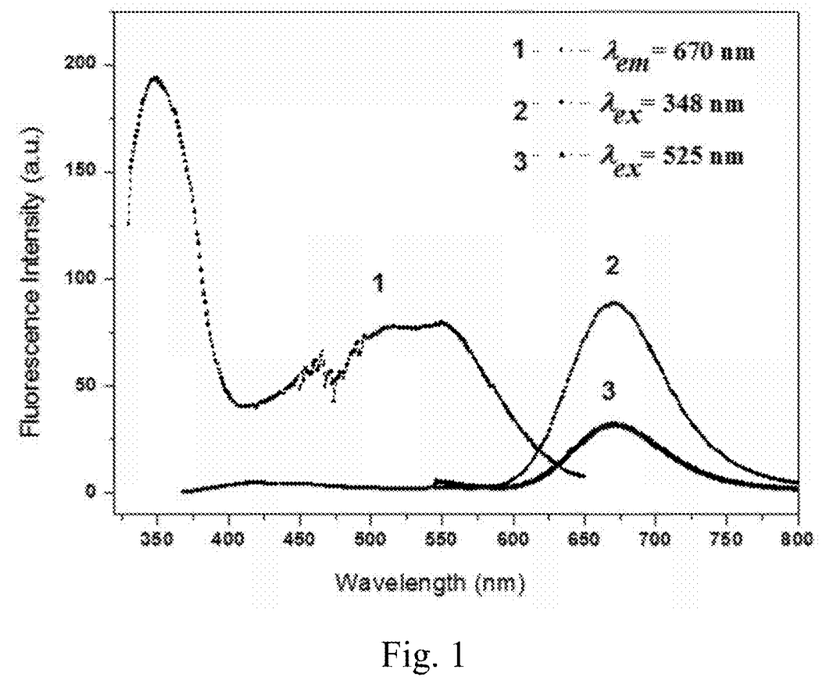
FIG. 1 shows the fluorescence emission spectra of the fluorescence sensing film and the excitation-emission spectra in solution by the present invention.

FIG. 1 is an excitation-emission spectrogram of the fluorescent compound and the fluorescent film prepared by the first embodiment, wherein: Ex and Em are excitation spectrum and emission spectrum of the fluorescent compound in the fluorescent film. It can be seen from FIG. 1 that a maximum excitation wavelength of the film is 348 nm and an emission wavelength is 670 nm.

Figure 2:
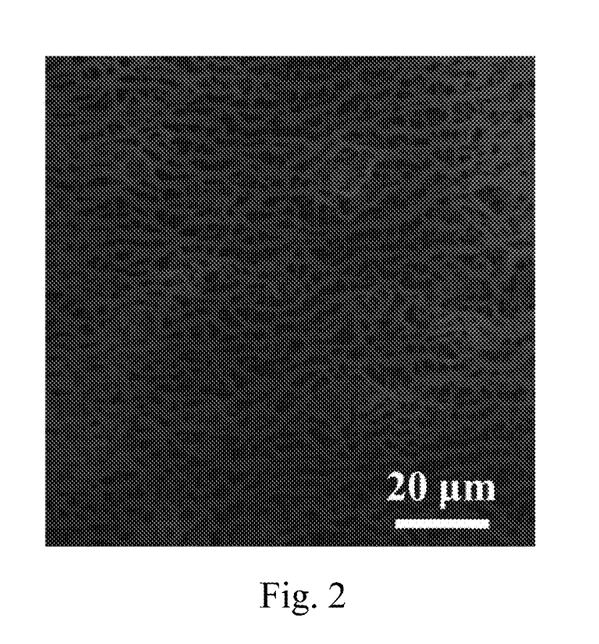
FIG. 2 is a microstructure diagram of a fluorescent sensing film prepared by the present invention.

FIG. 2 is a fluorescence micrograph of the fluorescent film prepared by the fluorescent compound according to the first embodiment. It can be seen from FIG. 2 that long alkyl chain is introduced to promote the film to form a fibrous network structure, which greatly increases the surface area of the film, and lays a solid foundation for quick and sensitive sensing; and moreover, good permeability provides a strong guarantee for the reversibility of sensing.

Figure 3:
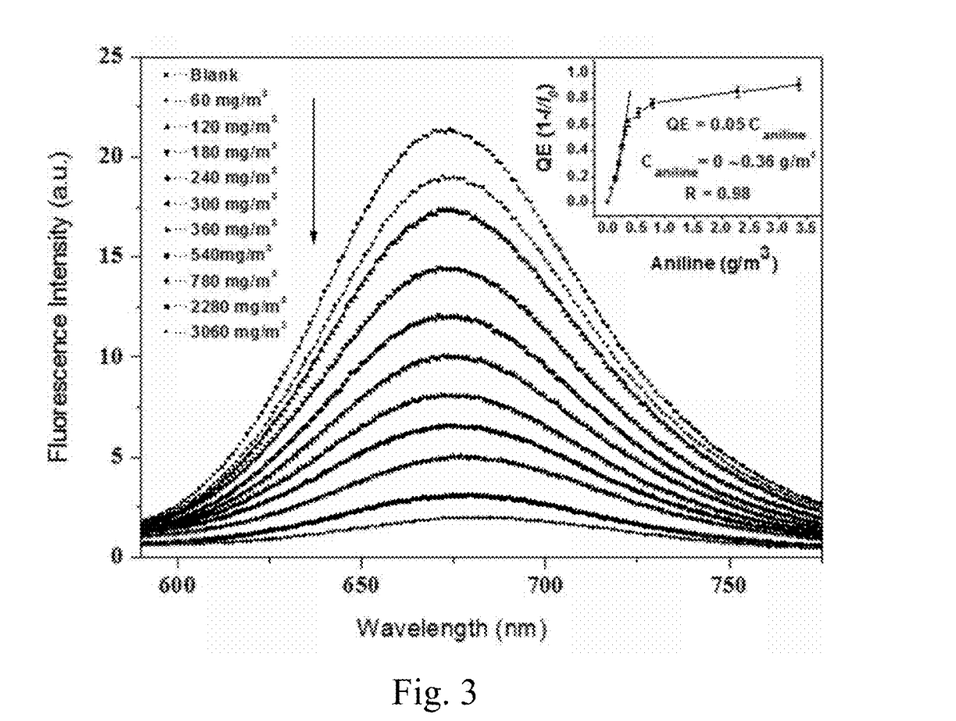
FIG. 3 is a fluorescent emission map of the fluorescent sensing film prepared by the present invention at different concentrations of aniline vapors.

FIG. 3 is a sensing map of the film response to different concentrations of aniline vapor according to the first embodiment. The concentrations of the measured aniline are respectively 60 mg/m$^3$, 120 mg/m$^3$, 180 mg/m$^3$, 240 mg/m$^3$, 300 mg/m$^3$, 360 mg/m$^3$, 540 mg/m$^3$, 780 mg/m$^3$, 2280 mg/m$^3$ and 3060 mg/m$^3$. In FIG. 3, the black curve is blank, other curves are fluorescent emission intensity curves corresponding to different concentrations of aniline vapors, wherein the former few groups of aniline vapor concentrations on the quenching efficiency of the film show a linear relationship, and then the latter groups gradually reach saturation. Therefore, it is proved that the film shows a high sensitivity to the detection of aniline vapors.

Figure 4:
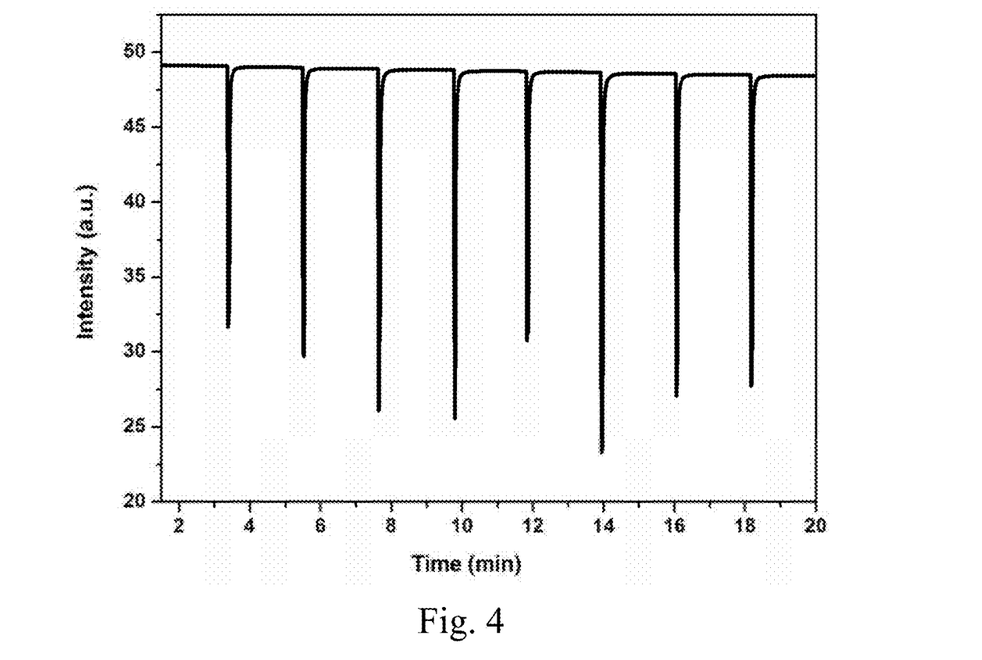
FIG. 4 is a restorative diagram of the fluorescent sensing film prepared by the present invention on a self-made instrument.

FIG. 4 is a restorative diagram of the film in response to a certain concentration of aniline vapor. It can be seen from FIG. 4 that the film responds very fast to the aniline vapor and is almost completely reversible, which creates favorable conditions for thin-film device formation.

Based on the above verification tests, it can be seen that the fluorescent sensing film prepared by the present invention has good photochemical stability and fluorescent characteristics, has uniform and controllable microstructure, high sensitivity for aniline vapor recognition and almost completely reversible detection. Therefore, it is very suitable for preparing fluorescent sensor devices.

Second Embodiment (1) respectively dissolving 0.57 g of 1,4,5,8-naphthalenetetracarboxylic dianhydride and 0.93 g of dibromo isocyanuric acid into 50 mL of oleum with a concentration of 20%, and then sufficiently uniformly stirring at room temperature for 2 h, adding the oleum dissolved with the dibromo isocyanuric acid into the oleum dissolved with the 1,4,5,8-naphthalenetetracarboxylic dianhydride drop by drop for 1 h, and then continuously stirring and reacting at 90° C. for 24 h, obtaining a mixed solution, uniformly stirring for 30 min after pouring the mixed solution into crushed ice, obtaining a precipitate, sucking and filtering the obtained precipitate, drying under vacuum after washing a sucked and filtered intermediate product with water for 3 times, and obtaining a first compound, wherein: a molar ratio of the 1,4,5,8-naphthalenetetracarboxylic dianhydride to the dibromo isocyanuric acid is 1:1.5, and a molar ratio of the oleum dissolved with the dibromo isocyanuric acid to the oleum dissolved with the 1,4,5,8-naphthalenetetracarboxylic dianhydride is 1:1;

(2) dissolving 0.1 g of the first compound into 25 mL of glacial acetic acid under nitrogen protection, and then stirring at room temperature for 30 min, adding 120 μL of a seventh compound after sufficiently dissolving the first compound, continuously stirring at 120° C. for 3 h, dissolving an obtained precipitate into ice water and stirring for 30 min, obtaining a solid precipitate, sucking and filtering the obtained solid precipitate, drying under vacuum after washing a sucked and filtered intermediate product with water for 3 times, and then performing column chromatography separation, and obtaining a second compound, wherein: a molar ratio of the first compound, the seventh compound and the glacial acetic acid is 1:3:360, the column chromatography separation is performed with an eluent prepared by mixing dichloromethane and petroleum ether with a volume ratio of 1:1, in here, the seventh compound is m=4;

(3) dissolving 0.09 g of the second compound, 0.059 g of benzenamine,4-ethynyl-, 0.001 g of tetrakistriphenylphosphine palladium and 0.00132 g of cuprous iodide into a mixed solvent of 14 mL of toluene and 6 mL of diisopropylamine under water-free and oxygen-free condition, and then stirring and reacting at 70° C. for 48 h, obtaining a mixture, washing the obtained mixture with saturated ammonium chloride solution for 3 times, and then washing with saturated sodium bicarbonate solution for 3 times, and then washing with saturated sodium chloride aqueous solution for 3 times, drying under vacuum after drying a washed intermediate product in a hanging manner, and then performing column chromatography separation, and obtaining a third compound, wherein:

a preferable molar ratio of the second compound, the benzenamine,4-ethynyl-, the tetrakistriphenylphosphine palladium, the cuprous iodide, the toluene and the diisopropylamine is 1:3:0.05:0.05:920:300, the column chromatography separation is performed with an eluent prepared by mixing tetrahydrofuran with petroleum ether with a volume ratio of 1:3;

(4) dissolving 2 g of methyl trihydroxybenzoate into 50 mL of N,N-dimethylformamide under water-free and oxygen-free condition, and then adding 15 g of potassium carbonate and 0.2 g of potassium iodide in sequence, adding 13 mL of brominated alkane reagent after stirring at 120° C. for 2 h, continuously stirring at 150° C. for 48 h, obtaining a precipitate, washing with ethyl acetate for 3 times after sucking and filtering the precipitate, obtaining a filtrate, refrigerating the filtrate, and then separating white solid out, and obtaining a fourth compound, wherein:

a molar ratio of the methyl trihydroxybenzoate, the brominated alkane reagent, the potassium carbonate, the potassium iodide and the N,N-dimethylformamide is 1:4:10:0.05:80, in here, n is equal to 12;

(5) dissolving 0.5 g of the fourth compound into 17 mL of ethanol, and then adding 0.5 g of potassium hydroxide, reflux-stirring at 80° C. for 8 h, diluting a stirred solution with water, acidizing a diluted solution with hydrochloric acid having a concentration of 1 mol/L to pH=1, obtaining a precipitate, sucking and filtering the precipitate, drying after washing a sucked and filtered intermediate product with water for 3 times, and obtaining a fifth compound, wherein:

a molar ratio of the fourth compound, the potassium hydroxide and the ethanol is 1:2.5:380;

(6) adding 0.1 g of the fifth compound into 20 mL of toluene under nitrogen protection, and then adding 1.8 mL of thionylchloride ($SOCl_2$), reflux-stirring for 4 h, removing excess thionylchloride ($SOCl_2$) with toluene for 3 times, and obtaining a sixth compound, wherein:

a molar ratio of the fifth compound, the thionylchloride ($SOCl_2$) and the toluene is 1:6:1000; and

(7) dissolving 2.57 g of the sixth compound, 0.34 g of EDC and 0.01 g of DMAP into 25 mL of redistilled toluene solution under nitrogen protection, and then stirring at room temperature for 30 min, obtaining a mixed solution, adding 0.53 g of the third compound into the mixed solution, continuously stirring and reacting at room temperature for 12 h, and then washing with water for 3 times, and then removing solvent from a reacted solution, drying under vacuum, performing column chromatography separation, and finally obtaining the fluorescent compound having the sensing ability to the aniline and the o-toluidine, wherein:

a molar ratio of the third compound, the sixth compound, the EDC and the DMAP is 1:3:0.1:0.2, the column chromatography separation is performed with an eluent prepared by dichloromethane.

Third Embodiment (1) respectively dissolving 0.57 g of 1,4,5,8-naphthalenetetracarboxylic dianhydride and 0.62 g of dibromo isocyanuric acid into 50 mL of oleum with a concentration of 20%, and then sufficiently uniformly stirring at room temperature for 2 h, adding the oleum dissolved with the dibromo isocyanuric acid into the oleum dissolved with the 1,4,5,8-naphthalenetetracarboxylic dianhydride drop by drop for 1 h, and then continuously stirring and reacting at 90° C. for 24 h, obtaining a mixed solution, uniformly stirring for 30 min after pouring the mixed solution into crushed ice, obtaining a precipitate, sucking and filtering the obtained precipitate, drying under vacuum after washing a sucked and filtered intermediate product with water for 3 times, and obtaining a first compound, wherein: a molar ratio of the 1,4,5,8-naphthalenetetracarboxylic dianhydride to the dibromo isocyanuric acid is 1:1, and a molar ratio of the oleum dissolved with the dibromo isocyanuric acid to the oleum dissolved with the 1,4,5,8-naphthalenetetracarboxylic dianhydride is 2:1;

(2) dissolving 0.1 g of the first compound into 28 mL of glacial acetic acid under nitrogen protection, and then stirring at room temperature for 30 min, adding 100 μL of a seventh compound after sufficiently dissolving the first compound, continuously stirring at 120° C. for 3 h, dissolving an obtained precipitate into ice water and stirring for 30 min, obtaining a solid precipitate, sucking and filtering the obtained solid precipitate, drying under vacuum after washing a sucked and filtered intermediate product with water for 3 times, and then performing column chromatography separation, and obtaining a second compound, wherein: a molar ratio of the first compound, the seventh compound and the glacial acetic acid is 1:2.5:400, the column chromatography separation is performed with an eluent prepared by mixing dichloromethane and petroleum ether with a volume ratio of 1:1, in here, the seventh compound is m=4

(3) dissolving 0.09 g of the second compound, 0.049 g of benzenamine,4-ethynyl-, 0.001 g of tetrakistriphenylphosphine palladium and 0.00132 g of cuprous iodide into a mixed solvent of 15 mL of toluene and 6 mL of diisopropylamine under water-free and oxygen-free condition, and then stirring and reacting at 70° C. for 48 h, obtaining a mixture, washing the obtained mixture with saturated ammonium chloride solution for 3 times, and then washing with saturated sodium bicarbonate solution for 3 times, and then washing with saturated sodium chloride aqueous solution for 3 times, drying under vacuum after drying a washed intermediate product in a hanging manner, and then performing column chromatography separation, and obtaining a third compound, wherein:

a preferable molar ratio of the second compound, the benzenamine,4-ethynyl-, the tetrakistriphenylphosphine palladium, the cuprous iodide, the toluene and the diisopropylamine is 1:2.5:0.05:0.05:950:300, the column chromatography separation is performed with an eluent prepared by mixing tetrahydrofuran with petroleum ether with a volume ratio of 1:3;

(4) dissolving 2 g of methyl trihydroxybenzoate into 63 mL of N,N-dimethylformamide under water-free and oxygen-free condition, and then adding 15 g of potassium carbonate and 0.2 g of potassium iodide in sequence, adding 10 mL of brominated alkane reagent after stirring at 120° C. for 2 h, continuously stirring at 150° C. for 48 h, obtaining a precipitate, washing with ethyl acetate for 3 times after sucking and filtering the precipitate, obtaining a filtrate, refrigerating the filtrate, and then separating white solid out, and obtaining a fourth compound, wherein:

a molar ratio of the methyl trihydroxybenzoate, the brominated alkane reagent, the potassium carbonate, the potassium iodide and the N,N-dimethylformamide is 1:3:10:0.05:100, in here, n is equal to 12;

(5) dissolving 0.5 g of the fourth compound into 20 mL of ethanol, and then adding 0.4 g of potassium hydroxide, reflux-stirring at 80° C. for 8 h, diluting a stirred solution with water, acidizing a diluted solution with hydrochloric acid having a concentration of 1 mol/L to pH=1, obtaining a precipitate, sucking and filtering the precipitate, drying after washing a sucked and filtered intermediate product with water for 3 times, and obtaining a fifth compound, wherein:

a molar ratio of the fourth compound, the potassium hydroxide and the ethanol is 1:2:400;

(6) adding 0.1 g of the fifth compound into 16 mL of toluene under nitrogen protection, and then adding 1.5 mL of thionylchloride (SOCl$_2$), reflux-stirring for 4 h, removing excess thionylchloride (SOCl$_2$) with toluene for 3 times, and obtaining a sixth compound, wherein:

a molar ratio of the fifth compound, the thionylchloride (SOCl$_2$) and the toluene is 1:5:800; and

(7) dissolving 1.285 g of the sixth compound, 0.34 g of 0.34 g of EDC and 0.02 g of DMAP into 25 mL of redistilled toluene solution under nitrogen protection, and then stirring at room temperature for 30 min, obtaining a mixed solution, adding 0.53 g of the third compound into the mixed solution, continuously stirring and reacting at room temperature for 12 h, and then washing with water for 3 times, and then removing solvent from a reacted solution, drying under vacuum, performing column chromatography separation, and finally obtaining the fluorescent compound having the sensing ability to the aniline and the o-toluidine, wherein:

a molar ratio of the third compound, the sixth compound, the EDC and the DMAP is 1:1.5:0.1:0.4, the column chromatography separation is performed with an eluent prepared by dichloromethane.

Fourth Embodiment (1) respectively dissolving 0.57 g of 1,4,5,8-naphthalenetetracarboxylic dianhydride and 0.62 g of dibromo isocyanuric acid into 50 mL of oleum with a concentration of 20%, and then sufficiently uniformly stirring at room temperature for 4 h, adding the oleum dissolved with the dibromo isocyanuric acid into the oleum dissolved with the 1,4,5,8-naphthalenetetracarboxylic dianhydride drop by drop for 1 h, and then continuously stirring and reacting at 90° C. for 36 h, obtaining a mixed solution, uniformly stirring for 30 min after pouring the mixed solution into crushed ice, obtaining a precipitate, sucking and filtering the obtained precipitate, drying under vacuum after washing a sucked and filtered intermediate product with water for 3 times, and obtaining a first compound, wherein: a molar ratio of the 1,4,5,8-naphthalenetetracarboxylic dianhydride to the dibromo isocyanuric acid is 1:1 and a molar ratio of the oleum dissolved with the dibromo isocyanuric acid to the oleum dissolved with the 1,4,5,8-naphthalenetetracarboxylic dianhydride is 1:1;

(2) dissolving 0.1 g of the first compound into 25 mL of glacial acetic acid under nitrogen protection, and then stirring at room temperature for 1 h, adding 100 µL of a seventh compound after sufficiently dissolving the first compound, continuously stirring at 80° C. for 3 h, dissolving an obtained precipitate into ice water and stirring for 30 min, obtaining a solid precipitate, sucking and filtering the obtained solid precipitate, drying under vacuum after washing a sucked and filtered intermediate product with water for 3 times, and then performing column chromatography separation, and obtaining a second compound, wherein: a molar ratio of the first compound, the seventh compound and the glacial acetic acid is 1:2.5:360, the column chromatography separation is performed by an eluent prepared by mixing dichloromethane and petroleum ether with a volume ratio of 1:1, in here, the seventh compound is m=4;

(3) dissolving 0.09 g of the second compound, 0.049 g of benzenamine,4-ethynyl-, 0.001 g of tetrakistriphenylphosphine palladium and 0.00132 g of cuprous iodide into a mixed solvent of 14 mL of toluene and 6 mL of diisopropylamine under water-free and oxygen-free condition, and then stirring and reacting at 50° C. for 48 h, obtaining a mixture, washing the obtained mixture with saturated ammonium chloride solution for 3 times, and then washing with saturated sodium bicarbonate solution for 3 times, and then washing with saturated sodium chloride aqueous solution for 3 times, drying under vacuum after drying a washed intermediate product in a hanging manner, and then performing column chromatography separation, and obtaining a third compound, wherein:

a preferable molar ratio of the second compound, the benzenamine,4-ethynyl-, the tetrakistriphenylphosphine palladium, the cuprous iodide, the toluene and the diisopropylamine is 1:2.5:0.05:0.05:920:300, the column chromatography separation is performed with an eluent prepared by mixing tetrahydrofuran with petroleum ether with a volume ratio of 1:3;

(4) dissolving 2 g of methyl trihydroxybenzoate into 50 mL of N,N-dimethylformamide under water-free and oxygen-free condition, and then adding 15 g of potassium carbonate and 0.2 g of potassium iodide in sequence, adding 10 mL of brominated alkane reagent after stirring at 150° C. for 2 h, continuously stirring at 150° C. for 48 h, obtaining a precipitate, washing with ethyl acetate for 3 times after sucking and filtering the precipitate, obtaining a filtrate, refrigerating the filtrate, and then separating white solid out, and obtaining a fourth compound, wherein:

a molar ratio of the methyl trihydroxybenzoate, the brominated alkane reagent, the potassium carbonate, the potassium iodide and the N,N-dimethylformamide is 1:3:10:0.05:80, in here, n is equal to 12;

(5) dissolving 0.5 g of the fourth compound into 17 mL of ethanol, and then adding 0.4 g of potassium hydroxide, reflux-stirring at 60° C. for 8 h, diluting a stirred solution with water, acidizing a diluted solution with hydrochloric acid having a concentration of 1 mol/L to pH=1, obtaining a precipitate, sucking and filtering the precipitate, drying after washing a sucked and filtered intermediate product with water for 3 times, and obtaining a fifth compound, wherein:

a molar ratio of the fourth compound, the potassium hydroxide and the ethanol is 1:2:380;

(6) adding 0.1 g of the fifth compound into 20 mL of toluene under nitrogen protection, and then adding 1.5 mL of thionylchloride (SOCl$_2$), reflux-stirring for 4 h, removing excess thionylchloride (SOCl$_2$) with toluene for 1 time, and obtaining a sixth compound, wherein:

a molar ratio of the fifth compound, the thionylchloride (SOCl$_2$) and the toluene is 1:5:1000; and (7) dissolving 1.285 g of the sixth compound, 0.34 g of EDC and 0.01 g of DMAP into 25 mL of redistilled toluene solution under nitrogen protection, and then stirring at room temperature for 30 min, obtaining a mixed solution, adding 0.53 g of the third compound into the mixed solution, continuously stirring and reacting at room temperature for 8 h, and then washing with water for 3 times, and then removing solvent from a reacted solution, drying under vacuum, performing column chromatography separation, and finally obtaining the fluorescent compound having the sensing ability to the aniline and the o-toluidine, wherein:

a molar ratio of the third compound, the sixth compound, the EDC and the DMAP is 1:1.5:0.1:0.2, the column chromatography separation is performed with an eluent prepared by dichloromethane.

Fifth Embodiment

A method for preparing a fluorescent sensing film having a sensing ability to aniline and o-toluidine according to a fifth embodiment of the present invention comprises steps as follows:

In the step (2) of the first embodiment, dissolving 0.1 g of the first compound into 25 mL of glacial acetic acid under nitrogen protection, and then stirring at room temperature for 30 min, adding 100 μL of a seventh compound after sufficiently dissolving the first compound, continuously stirring at 120° C. for 3 h, dissolving an obtained precipitate into ice water and stirring for 30 min, obtaining a solid precipitate, sucking and filtering the obtained solid precipitate, drying under vacuum after washing a sucked and filtered intermediate product with water for 3 times, and then performing column chromatography separation, and obtaining a second compound, wherein: a molar ratio of the first compound, the seventh compound and the glacial acetic acid is 1:2.5:360, the column chromatography separation is performed with an eluent prepared by mixing dichloromethane and petroleum ether with a volume ratio of 1:1, in here, the seventh compound is m=5, In the step (3) of the first embodiment, dissolving 0.09 g of the second compound, 0.06 g of benzenamine,4-ethynyl-, 0.001 g of tetrakistriphenylphosphine palladium and 0.00132 g of cuprous iodide into a mixed solvent of 14 mL of toluene and 6 mL of diisopropylamine under water-free and oxygen-free condition, and then stirring and reacting at 70° C. for 48 h, obtaining a mixture, washing the obtained mixture with saturated ammonium chloride solution for 3 times, and then washing with saturated sodium bicarbonate solution for 3 times, and then washing with saturated sodium chloride aqueous solution for 3 times, drying under vacuum after drying a washed intermediate product in a hanging manner, and then performing column chromatography separation, and obtaining a third compound, wherein:

a preferable molar ratio of the second compound, the benzenamine,4-ethynyl-, the tetrakistriphenylphosphine palladium, the cuprous iodide, the toluene and the diisopropylamine is 1:3:0.05:0.05:920:300, the column chromatography separation is performed with an eluent prepared by mixing tetrahydrofuran and petroleum ether with a volume ratio of 1:3.

Other steps of the fifth embodiment are as same as those of the first embodiment to prepare the sensing film.

Sixth Embodiment

A method for preparing a fluorescent sensing film having a sensing ability to aniline and o-toluidine according to a sixth embodiment of the present invention comprises steps as follows:

In the step (2) of the first embodiment, dissolving 0.1 g of the first compound into 25 mL of glacial acetic acid under nitrogen protection, and then stirring at room temperature for 30 min, adding 100 μL of a seventh compound after sufficiently dissolving the first compound, continuously stirring at 120° C. for 3 h, dissolving an obtained precipitate into ice water and stirring for 30 min, obtaining a solid precipitate, sucking and filtering the obtained solid precipitate, drying under vacuum after washing a sucked and filtered intermediate product with water for 3 times, and then performing column chromatography separation, and obtaining a second compound, wherein: a molar ratio of the first compound, the seventh compound and the glacial acetic acid is 1:2.5:360, the column chromatography separation is performed with an eluent prepared by mixing dichloromethane and petroleum ether with a volume ratio of 1:1, in here, the seventh compound is m=5;

In the step (3) of the first embodiment, dissolving 0.09 g of the second compound, 0.049 g of benzenamine,4-ethynyl-, 0.001 g of tetrakistriphenylphosphine palladium and 0.00132 g of cuprous iodide into a mixed solvent of 14 mL of toluene and 6 mL of diisopropylamine under water-free and oxygen-free condition, and then stirring and reacting at 70° C. for 48 h, obtaining a mixture, washing the obtained mixture with saturated ammonium chloride solution for 3 times, and then washing with saturated sodium bicarbonate solution for 3 times, and then washing with saturated sodium chloride aqueous solution for 3 times, drying under vacuum after drying a washed intermediate product in a hanging manner, and then performing column chromatography separation, and obtaining a third compound, wherein:

a preferable molar ratio of the second compound, the benzenamine,4-ethynyl-, the tetrakistriphenylphosphine palladium, the cuprous iodide, the toluene and the diisopropylamine is 1:2.5:0.05:0.05:920:300, the column chromatography separation is performed with an eluent prepared by mixing tetrahydrofuran with petroleum ether with a volume ratio of 1:2.

Other steps of the sixth embodiment are as same as those of the first embodiment to prepare the sensing film.

Seventh Embodiment

A method for preparing a fluorescent sensing film having a sensing ability to aniline and o-toluidine according to a seventh embodiment of the present invention comprises steps as follows:

In the step (4) of the first embodiment, dissolving 2 g of methyl trihydroxybenzoate into 50 mL of N,N-dimethylformamide under water-free and oxygen-free condition, and then adding 15 g of potassium carbonate and 0.2 g of potassium iodide in sequence, adding 10 mL of brominated alkane reagent after stirring at 120° C. for 2 h, continuously stirring at 150° C. for 48 h, obtaining a precipitate, washing with ethyl acetate for 3 times after sucking and filtering the precipitate, obtaining a filtrate, refrigerating the filtrate, and then separating white solid out, and obtaining a fourth compound, wherein:

a molar ratio of the methyl trihydroxybenzoate, the brominated alkane reagent, the potassium carbonate, the potassium iodide and the N,N-dimethylformamide is 1:3:10:0.05:80, in here, n is equal to 16.

Other steps of the seventh embodiment are as same as those of the first embodiment to prepare the sensing film.

Eighth Embodiment

In the step (4) of the first embodiment, dissolving 2 g of methyl trihydroxybenzoate into 50 mL of N,N-dimethylformamide under water-free and oxygen-free condition, and then adding 15 g of potassium carbonate and 0.2 g of potassium iodide in sequence, adding 13.5 mL of brominated alkane reagent after stirring at 120° C. for 2 h, continuously stirring at 150° C. for 48 h, obtaining a precipitate, washing with ethyl acetate for 3 times after sucking and filtering the precipitate, obtaining a filtrate, refrigerating the filtrate, and then separating white solid out, and obtaining a fourth compound, wherein:

a molar ratio of the methyl trihydroxybenzoate, the brominated alkane reagent, the potassium carbonate, the potassium iodide and the N,N-dimethylformamide is 1:4:10:0.05:80, in here, n is equal to 16.

Ninth Embodiment

A method for preparing a fluorescent sensing film having a sensing ability to aniline and o-toluidine according to a ninth embodiment of the present invention comprises steps as follows:

In the step (1) of the first embodiment, respectively dissolving 0.57 g of 1,4,5,8-naphthalenetetracarboxylic dianhydride and 0.62 g of dibromo isocyanuric acid into 100 mL of oleum with a concentration of 20%, and then sufficiently uniformly stirring at room temperature for 2 h, adding the oleum dissolved with the dibromo isocyanuric acid into the oleum dissolved with the 1,4,5,8-naphthalenetetracarboxylic dianhydride drop by drop for 1 h, and then continuously stirring and reacting at 50° C. for 36 h, obtaining a mixed solution, uniformly stirring for 30 min after pouring the mixed solution into crushed ice, obtaining a precipitate, sucking and filtering the obtained precipitate, drying under vacuum after washing a sucked and filtered intermediate product with water for 3 times, and obtaining a first compound, wherein: a molar ratio of the 1,4,5,8-naphthalenetetracarboxylic dianhydride to the dibromo isocyanuric acid is 1:1, and a molar ratio of the oleum dissolved with the dibromo isocyanuric acid to the oleum dissolved with the 1,4,5,8-naphthalenetetracarboxylic dianhydride is 1:1.

Other steps of the ninth embodiment are as those of the first embodiment to prepare the sensing film.

Tenth Embodiment

Dissolving a compound having a sensing ability to aniline and o-toluidine into methyl cyclohexane, obtaining a stock solution with a concentration of $1\times10^4$ mol/L, uniformly spin-coating the stock solution with a volume of 15 μL onto a clean and activated glass substrate surface, and then standing at room temperature for 6 h, and then naturally drying at room temperature for 24 h, obtaining the fluorescent sensing film, and sealing for standby application.

Other steps of the tenth embodiment are as those of the first embodiment to prepare the sensing film.

Eleventh Embodiment

Dissolving a compound having a sensing ability to aniline and o-toluidine into methyl cyclohexane, obtaining a stock solution with a concentration of $5\times10^{-4}$ mol/L, uniformly spin-coating the stock solution with a volume of 10 μL onto a clean and activated glass substrate surface, and then standing at room temperature for 6 h, and then naturally drying at room temperature for 24 h, obtaining the fluorescent sensing film, and sealing for standby application.

Other steps of the eleventh embodiment are as same as those of the first embodiment to prepare the sensing film.

Twelfth Embodiment

Dissolving a compound having a sensing ability to aniline and o-toluidine into methyl cyclohexane, obtaining a stock solution with a concentration of $5\times10^{-4}$ mol/L, uniformly spin-coating the stock solution with a volume of 15 μL onto a clean and activated glass substrate surface, and then standing at room temperature for 4 h, and then naturally drying at room temperature for 24 h, obtaining the fluorescent sensing film, and sealing for standby application.

Other steps of the twelfth embodiment are as same as those of the first embodiment to prepare the sensing film.

The inventor uses the synthesized naphthalene diimide (NDI) derivative in the first embodiment to do a lot of exploration experiments. It is found that the prepared film is able to sensitively detect aniline and o-toluidine.

Based on the above experiments, the sensing film provided by the present invention has high fluorescence quantum yield, good photochemical stability and ultrafine fibered network micro-topography. The larger specific surface area and the dense network structure of the sensing film are conducive to the capture and adsorption of aniline, for further sensing the aniline and the o-toluidine, and meanwhile greatly improving response to aniline and o-toluidine vapors. Accordingly, the present invention has high sensitivity to the detection of aniline gas and is expected to find potential application in chemical plants and large crude oil companies. Therefore, through adjusting the gelling appearances of the compound in different solvents, the present invention obtains the sensing material whose topography is controllable, so as to further optimize the sensing performance of the sensing material. The present invention has great significance for the highly sensitive gas phase detection of aniline gas.

What is claimed is:
1. A fluorescent compound having a sensing ability to aniline and o-toluidine, wherein the fluorescent compound has a structural formula of:

wherein:

2. A method for preparing a fluorescent compound having a sensing ability to aniline and o-toluidine, which comprises steps of:

(1) preparing a first compound, which comprises:
dissolving 1,4,5,8-naphthalenetetracarboxylic dianhydride and dibromo isocyanuric acid into a first amount of oleum with a concentration of 20% and a second amount of oleum with a concentration of 20%, respectively, and then sufficiently uniformly stirring at room temperature, adding the second amount of oleum dissolved with the dibromo isocyanuric acid into the first amount of oleum dissolved with the 1,4,5,8-naphthalenetetracarboxylic dianhydride drop by drop, and then continuously stirring and reacting at 60-90° C. for 12-48 h, mixing, obtaining a mixed solution, uniformly stirring after pouring the mixed solution into crushed ice, and then vacuum filtering, washing, drying, and obtaining the first compound, wherein: a structural formula of the first compound is (2) preparing a second compound, which comprises:
dissolving the first compound into glacial acetic acid under nitrogen protection, and then uniformly stirring at room temperature, and then adding a seventh compound, reflux-stirring for 2-4 h, filtering and collecting a precipitate, dissolving the precipitate into ice water and sufficiently stirring, and then vacuum filtering, washing, drying, performing column chromatography separation, and obtaining the second compound, wherein: a structural formula of the second compound is a structural formula of the seventh compound is R—NH$_2$, R=

(3) preparing a third compound, which comprises:
dissolving the second compound, benzenamine,4-ethynyl-, tetrakistriphenylphosphine palladium and cuprous iodide into a mixed solvent of toluene and diisopropylamine under water-free and oxygen-free condition, and then stirring and reacting at 50-70° C. for 24-48 h, respectively extracting with saturated sodium chloride aqueous solution and water, spin-drying, performing column chromatography separation, and obtaining the third compound, wherein a structural formula of the third compound is

(4) preparing a fourth compound, which comprises:
dissolving methyl trihydroxybenzoate into N,N-dimethylformamide under water-free and oxygen-free condition, and then adding potassium carbonate and potassium iodide in sequence, adding brominated alkane after stirring at 80-120° C. for 30 min, continuously reflux-stirring for 24-48 h, filtering and collecting a precipitate, vacuum filtering and washing the precipitate, obtaining a filtrate, refrigerating the filtrate, and then separating white solid out, and obtaining the fourth compound, wherein a structural formula of the fourth compound is n=12 or 16;
(5) preparing a fifth compound, which comprises:
dissolving the fourth compound into ethanol, and then adding potassium hydroxide, reflux-stirring and reacting for 8-12 h, diluting a stirred and reacted solution with water, adjusting a pH value to 1, filtering and collecting a precipitate, vacuum filtering, washing and drying the precipitate, and obtaining the fifth compound, wherein a structural formula of the fifth compound is (6) preparing a sixth compound, which comprises:
adding the fifth compound into toluene under nitrogen protection, and then adding a catalytic amount of thionylchloride (SOCl$_2$), reflux-stirring and reacting for 4 h, and then removing excess thionylchloride (SOCl$_2$) and toluene, and obtaining the sixth compound, wherein a structural formula of the sixth compound is and
(7) dissolving the sixth compound, N1-((ethylimino) methylene)-N3,N3-dimethylpropane-1,3-diamine (EDC) and 4-dimethylaminopyridine (DMAP) into redistilled toluene solution under nitrogen protection, and then adding the third compound after stirring and reacting for 30 min, continuously stirring and reacting at room temperature for 12-20 h, and then washing with water, obtaining a reacted solution, drying after removing solvent from the reacted solution, performing column chromatography separation, and finally obtaining the fluorescent compound, wherein a structural formula of the fluorescent compound is 3. The method for preparing the fluorescent compound having the sensing ability to the aniline and the o-toluidine, as recited in claim 2, wherein in the step (1), a molar ratio of the 1,4,5,8-naphthalenetetracarboxylic dianhydride to the dibromo isocyanuric acid is 1:(1-1.5), a molar ratio of the first amount of oleum to the second amount of oleum is 1:1.

4. The method for preparing the fluorescent compound having the sensing ability to the aniline and the o-toluidine, as recited in claim 3, wherein in the step (2), a molar ratio of the first compound, the seventh compound and the glacial acetic acid is 1:(2.5-3):(300-400); the column chromatography separation is performed using an eluent prepared by mixing dichloromethane and petroleum ether with a volume ratio of 1:1.

5. The method for preparing the fluorescent compound having the sensing ability to the aniline and the o-toluidine, as recited in claim 4, wherein in the step (3), a molar ratio of the second compound, the benzenamine,4-ethynyl-, the tetrakistriphenylphosphine palladium and the cuprous iodide is 1:(2-3):(0.05-0.1):(0.05-0.1); a volume ratio of the toluene to the diisopropylamine in the mixed solvent is 7:3; the column chromatography separation is performed using an eluent prepared by mixing tetrahydrofuran and petroleum ether with a volume ratio of 1:3.

6. The method for preparing the fluorescent compound having the sensing ability to the aniline and the o-toluidine, as recited in claim 5, wherein in the step (4), a molar ratio of the methyl trihydroxybenzoate, the brominated alkane reagent, the potassium carbonate, the potassium iodide and the N,N-dimethylformamide is 1:(3-5):(10-15):0.05:(80-100); the pH value is adjusted through hydrochloric acid with a concentration of 1 mol/L.

7. The method for preparing the fluorescent compound having the sensing ability to the aniline and the o-toluidine, as recited in claim 6, wherein in the step (5), a molar ratio of the fourth compound, the potassium hydroxide and the ethanol is 1:(2-3):(350-400); in the step (6), a molar ratio of the fifth compound, the thionylchloride (SOCl$_2$) and the toluene is 1:(5-10):(1000-1500).

8. The method for preparing the fluorescent compound having the sensing ability to the aniline and the o-toluidine, as recited in claim 7, wherein in the step (7), a molar ratio of the third compound, the sixth compound, the EDC and the DMAP is 1:(1.5-3):(0.1-0.2):(0.2-0.4), the column chromatography separation is performed using dichloromethane as an eluent.

9. A preparation method of a fluorescent sensing device, which comprises applying a fluorescent sensing film, wherein the fluorescent sensing film is prepared with a fluorescent compound having a sensing ability to aniline and o-toluidine through a method which comprises steps of:
(1) dissolving the fluorescent compound having the sensing ability to the aniline and the o-toluidine into methyl cyclohexane, and obtaining a stock solution with a concentration of $5\times10^{-4}$ mol/L; and
(2) uniformly spin-coating the stock solution onto a surface of a glass substrate, and then standing for 4-12 h, and obtaining the fluorescent sensing film, wherein the fluorescent compound has a structural formula of:

here, n=12, n=16,

* * * * *